(12) United States Patent
Talbert et al.

(10) Patent No.: US 11,622,677 B2
(45) Date of Patent: Apr. 11, 2023

(54) SYSTEMS, METHODS, AND DEVICES FOR PROVIDING ILLUMINATION IN AN ENDOSCOPIC IMAGING ENVIRONMENT

(71) Applicant: DePuy Synthes Products, Inc., Raynham, MA (US)

(72) Inventors: Joshua D. Talbert, Salt Lake City, UT (US); Jeremiah D. Henley, Salt Lake City, UT (US); Donald M. Wichern, Salt Lake City, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 424 days.

(21) Appl. No.: 15/855,921

(22) Filed: Dec. 27, 2017

(65) Prior Publication Data

US 2018/0177388 A1 Jun. 28, 2018

Related U.S. Application Data

(60) Provisional application No. 62/522,239, filed on Jun. 20, 2017, provisional application No. 62/439,330, filed on Dec. 27, 2016.

(51) Int. Cl.
*A61B 1/06* (2006.01)
*H04N 5/225* (2006.01)
(Continued)

(52) U.S. Cl.
CPC ........ *A61B 1/0646* (2013.01); *A61B 1/00006* (2013.01); *A61B 1/0017* (2013.01);
(Continued)

(58) Field of Classification Search
CPC .... H04N 5/2253; H04N 5/2256; H04N 5/374; H04N 5/2354; H04N 2005/2255;
(Continued)

(56) References Cited

U.S. PATENT DOCUMENTS

| 4,653,042 A | 3/1987 | d'Auria et al. |
| 5,408,265 A | 4/1995 | Sasaki |

(Continued)

FOREIGN PATENT DOCUMENTS

| CN | 110113982 A | 8/2019 |
| CN | 110113983 A | 8/2019 |

(Continued)

OTHER PUBLICATIONS

Computer translation of Japanese Publication No. JP2002040268A.

*Primary Examiner* — Nasim N Nirjhar
(74) *Attorney, Agent, or Firm* — Terrence J. Edwards; TechLaw Ventures, PLLC

(57) ABSTRACT

The disclosure relates to an endoscopic system. The system may include a single optical fiber. The system may further include a light source which transmits light into the single optical fiber. An image sensor may be provided within the endoscopic system and disposed at a distal end of the single optical fiber. The endoscopic system may be additionally fitted with a diffuser on the distal end of the single optical fiber which outputs a light cone that is broader than an output of the single optical fiber without the diffuser.

20 Claims, 9 Drawing Sheets

(51) Int. Cl.
  *H04N 5/374* (2011.01)
  *H04N 5/235* (2006.01)
  *A61B 1/00* (2006.01)
  *A61B 1/07* (2006.01)
  *A61B 1/05* (2006.01)
  *G02B 23/24* (2006.01)
  *A61B 1/04* (2006.01)
  *A61B 1/045* (2006.01)

(52) U.S. Cl.
  CPC ...... *A61B 1/00096* (2013.01); *A61B 1/00167* (2013.01); *A61B 1/044* (2022.02); *A61B 1/045* (2013.01); *A61B 1/05* (2013.01); *A61B 1/051* (2013.01); *A61B 1/063* (2013.01); *A61B 1/0615* (2013.01); *A61B 1/0623* (2013.01); *A61B 1/0625* (2022.02); *A61B 1/0638* (2013.01); *A61B 1/0655* (2022.02); *A61B 1/0669* (2013.01); *A61B 1/07* (2013.01); *G02B 23/2469* (2013.01); *H04N 5/2253* (2013.01); *H04N 5/2256* (2013.01); *H04N 5/2354* (2013.01); *H04N 5/374* (2013.01); *H04N 2005/2255* (2013.01)

(58) Field of Classification Search
  CPC ......... A61B 1/045; A61B 1/0638; A61B 1/04; A61B 1/05; A61B 1/00096; A61B 1/07; A61B 1/0646; A61B 1/0669; A61B 1/00006; A61B 1/051; A61B 1/063
  See application file for complete search history.

(56) References Cited

U.S. PATENT DOCUMENTS

| | | | |
|---|---|---|---|
| 5,572,016 A | 11/1996 | Wood et al. | |
| 5,681,632 A | 10/1997 | Kitaura et al. | |
| 5,751,869 A | 5/1998 | Li et al. | |
| 6,178,346 B1* | 1/2001 | Amundson | A61B 5/0086 348/77 |
| 6,485,414 B1 | 11/2002 | Neuberger | |
| 6,937,331 B1 | 8/2005 | Nguyen | |
| 10,506,142 B2 | 12/2019 | Talbert et al. | |
| 2002/0028041 A1 | 3/2002 | Easley | |
| 2002/0161282 A1 | 10/2002 | Fulghum | |
| 2002/0170289 A1 | 11/2002 | Hayashi et al. | |
| 2007/0100205 A1 | 5/2007 | Iriyama | |
| 2008/0039715 A1* | 2/2008 | Wilson | A61B 5/06 600/424 |
| 2008/0159736 A1 | 7/2008 | Kamijima | |
| 2009/0009595 A1 | 1/2009 | Ishiwata et al. | |
| 2009/0312607 A1* | 12/2009 | Sunagawa | A61B 1/0638 600/160 |
| 2010/0053312 A1 | 3/2010 | Watanabe et al. | |
| 2010/0069713 A1 | 3/2010 | Endo et al. | |
| 2010/0168586 A1 | 7/2010 | Hillman et al. | |
| 2010/0286475 A1 | 11/2010 | Robertson | |
| 2011/0170289 A1 | 7/2011 | Allen et al. | |
| 2012/0035422 A1 | 2/2012 | Lei et al. | |
| 2012/0155059 A1 | 6/2012 | Hoelen et al. | |
| 2013/0338436 A1* | 12/2013 | Dresher | A61B 1/06 600/109 |
| 2014/0008519 A1 | 1/2014 | Kameshima et al. | |
| 2014/0163319 A1 | 6/2014 | Blanquart et al. | |
| 2014/0184857 A1 | 7/2014 | Stokes et al. | |
| 2015/0065802 A1 | 3/2015 | Ozawa et al. | |
| 2015/0116561 A1 | 4/2015 | Takei | |
| 2015/0185414 A1* | 7/2015 | Baumann | A61B 1/00006 362/553 |
| 2016/0170218 A1 | 6/2016 | Johnson et al. | |
| 2016/0178533 A1* | 6/2016 | Gladnick | G02B 23/26 356/241.4 |
| 2016/0187600 A1* | 6/2016 | Viering | A61B 1/00126 600/182 |
| 2016/0227992 A1 | 8/2016 | Yoshino | |
| 2017/0042414 A1* | 2/2017 | Ito | H04N 5/225 |
| 2017/0095144 A1* | 4/2017 | Tabata | A61B 1/06 |
| 2017/0112370 A1* | 4/2017 | Daidoji | A61B 1/06 |
| 2017/0188803 A1 | 7/2017 | Yabe et al. | |
| 2017/0209032 A1 | 7/2017 | Matsunobu et al. | |
| 2017/0258307 A1 | 9/2017 | Daidoji et al. | |
| 2017/0340195 A1 | 11/2017 | Daidoji et al. | |
| 2020/0120243 A1 | 4/2020 | Talbert et al. | |

FOREIGN PATENT DOCUMENTS

| | | |
|---|---|---|
| CN | 110167419 A | 8/2019 |
| EP | 2457496 A1 | 5/2012 |
| EP | 2954836 A1 | 12/2015 |
| JP | 2002-040268 A | 2/2002 |
| WO | 2016056388 A1 | 4/2016 |
| WO | 2016084201 A1 | 6/2016 |
| WO | 2016132535 A1 | 8/2016 |
| WO | 2018125935 A1 | 5/2018 |
| WO | 2018125936 A1 | 5/2018 |
| WO | 2018125937 A1 | 5/2018 |

* cited by examiner

SYSTEMS, METHODS, AND DEVICES FOR PROVIDING ILLUMINATION IN AN ENDOSCOPIC IMAGING ENVIRONMENT

CROSS REFERENCE TO RELATED APPLICATIONS

This application claims the benefit of U.S. Provisional Application No. 62/439,330, filed Dec. 27, 2016, and U.S. Provisional Application No. 62/522,239, filed Jun. 20, 2017, which are incorporated herein by reference in their entirety, including but not limited to those portions that specifically appear hereinafter, the incorporation by reference being made with the following exception: In the event that any portion of the above-referenced provisional applications are inconsistent with this application, this application supersedes said above-referenced provisional applications.

TECHNICAL FIELD

The present disclosure relates generally to endoscopic imaging and more particularly relates to systems, methods and devices for providing illumination in an endoscopic imaging environment.

BACKGROUND

In endoscopic systems, artificial light must be provided for operation of an image sensor within an endoscope. Conventional endoscopic systems use a bundle of optical fibers to transmit light energy into a scene to provide an image sensor with enough light to capture an image. Unfortunately, conventional endoscopic systems are expensive and, therefore, must be used multiple times to justify the cost of their purchase. At the same time, however, conventional endoscopic systems must also be sterile such that no residue from a previous patient may infect a subsequent patient. Accordingly, significant safeguards must be put in place for reusable endoscopic systems to ensure that any endoscopic system will be completely sterilized, further increasing the cost of conventional endoscopic systems.

Another significant problem with conventional endoscopic systems is that, because at least some parts of an endoscopic system are inserted into a patient, larger diameter parts cause more damage to surrounding tissue or cause the patient discomfort. For example, in an arthroscopic environment, parts of an endoscopic system may be inserted into a patient's knee. Larger diameter parts result in larger wounds which adversely affect the patient's recovery. Similarly, in another environment, a patient may require an endoscopic inspection through an orifice in the patient's body. Larger diameter parts result in increased discomfort to the patient which may result in an inability to complete the examination or images of inadequate quality to ascertain any information from the examination.

Accordingly, it is desirable to provide an endoscopic system with both parts that are inexpensive and parts that are as small as technically viable. In this manner, endoscopic systems may be disposed of after a single use and may result in less tissue damage and/or discomfort to a patient. Thus, it is one object of this disclosure to provide an endoscopic system which includes a single optical fiber to illuminate a scene inside a patient's body to both reduce cost and diameter of parts of an endoscopic system that are inserted into a patient. It is a further object of this disclosure to provide an image sensor at a distal end of the single optical fiber. It is also an object of this disclosure to provide a diffuser, disposed at a distal end of the single optical fiber, which may output a light cone that is broader than an output of the single optical fiber without the diffuser.

SUMMARY

Disclosed herein is an endoscopic system. The system may include a single optical fiber. The system may further include a light source which transmits light into the single optical fiber. An image sensor may be provided within the endoscopic system and disposed at a distal end of the single optical fiber. The endoscopic system may be additionally fitted with a diffuser on the distal end of the single optical fiber which outputs a light cone that is broader than an output of the single optical fiber without the diffuser.

An endoscope may further be provided which includes a single optical fiber. The endoscope may further include an image sensor which may be disposed at a distal end of the single optical fiber. The endoscope may include a diffuser installed on the distal end of the single optical fiber which outputs a light cone that is broader than an output of the single optical fiber without the diffuser.

DETAILED DESCRIPTION

Imaging in a light deficient environment with optical image sensors (such as visible light CMOS or CCD or other imaging arrays) generally requires artificial illumination. With regard to endoscopic imaging, an endoscope often includes a tubular member, which may be inserted into a patient's body. A tip of the lumen may include an imaging sensor or other optical component for gathering light and capturing an image of a scene within the patient's body. Endoscopes must be sterile, due to their use in a body or during a medical procedure. Endoscopes or endoscopic components with sufficiently low price may be used as disposable or reposable components, which may reduce the costs and effort required by hospitals or medical personnel in sterilizing or managing the sterilization or state or reusable components.

The present disclosure presents systems, methods, and devices providing illumination in an endoscopic imaging environment that reduce expense and/or improve image quality for imaging in a light deficient environment. The methods, systems, and devices disclosed herein may be used in combination with or as alternatives to any of the teaching, technology, or functionality discussed and presented in one or more of: (1) U.S. Patent Application Publication No. US 2014/0163319 A1; (2) U.S. Pat. No. 9,509,917; and (3) U.S. Pat. No. 9,516,239, all of which are incorporated herein by this reference in their entireties.

A detailed description of systems and methods consistent with embodiments of the present disclosure is provided below. While several embodiments are described, it should be understood that this disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments may be practiced without some or all of these details. Moreover, for the purpose of clarity, certain technical material that is known in the related art has not been described in detail in order to avoid unnecessarily obscuring the disclosure.

Figure 1:
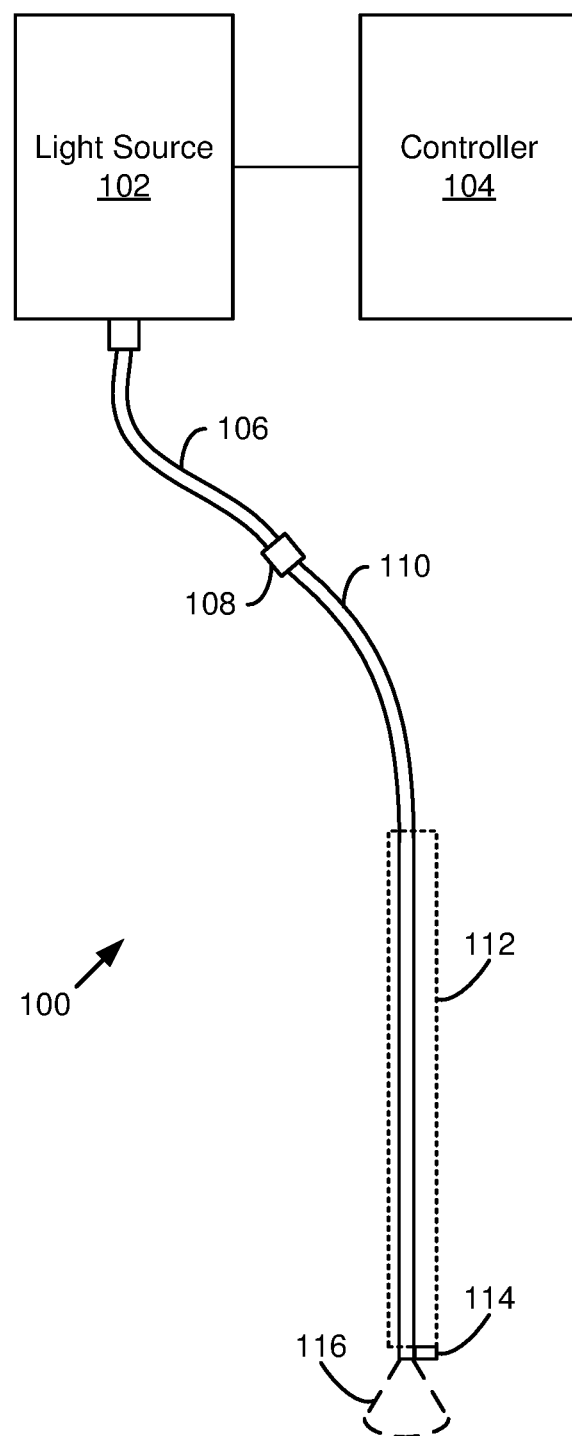
FIG. 1 is a schematic diagram illustrating a system for providing illumination to a light deficient environment, according to one embodiment.

Turning to the figures, FIG. 1 is a schematic diagram illustrating a system 100 for providing illumination to a light deficient environment, such as for endoscopic imaging. The system 100 includes a light source 102, a controller 104, a jumper waveguide 106, a coupler 108, a lumen waveguide 110, a lumen 112, and an image sensor 114 with accompanying optical components. The light source 102 generates light that travels through the jumper waveguide 106 and the lumen waveguide 110 to illuminate a scene at a distal end of the lumen 112. The lumen 112 may be inserted into a patient's body for imaging, such as during a procedure or examination. The light is output as illustrated by dashed lines 116. A scene illuminated by the light may be captured using the image sensor 114 and displayed for a doctor or other medical personnel. The controller 104 may provide control signals to the light source 102 to control when illumination is provided to a scene. If the image sensor 114 includes a CMOS sensor, light may be periodically provided to the scene in a series of illumination pulses between readout periods of the image sensor 114 during what is known as a blanking period. Thus, the light may be pulsed in a controlled manner to avoid overlapping into readout periods of the image pixels in a pixel array of the image sensor 114.

In one embodiment, the lumen waveguide 110 includes a plurality of optical fibers. The optical fibers may be made of a low cost material, such as plastic to allow for disposal of the lumen waveguide 110 and/or other portions of an endoscope. The jumper waveguide 106 may be permanently attached to the light source 102. For example, a jumper waveguide 106 may receive light from an emitter within the light source 102 and provide that light to the lumen waveguide 110 at the location of the coupler 108. In one embodiment, the jumper waveguide 106 may include one or more glass fibers. The jumper waveguide may include any other type of waveguide for guiding light to the lumen waveguide 110. The coupler 108 may couple the jumper waveguide 106 to the lumen waveguide 110 and allow light within the jumper waveguide 106 to pass to the lumen waveguide 110. In one embodiment, the lumen waveguide 110 may be directly coupled to a light source without any intervening jumper waveguide 106.

Figure 2:
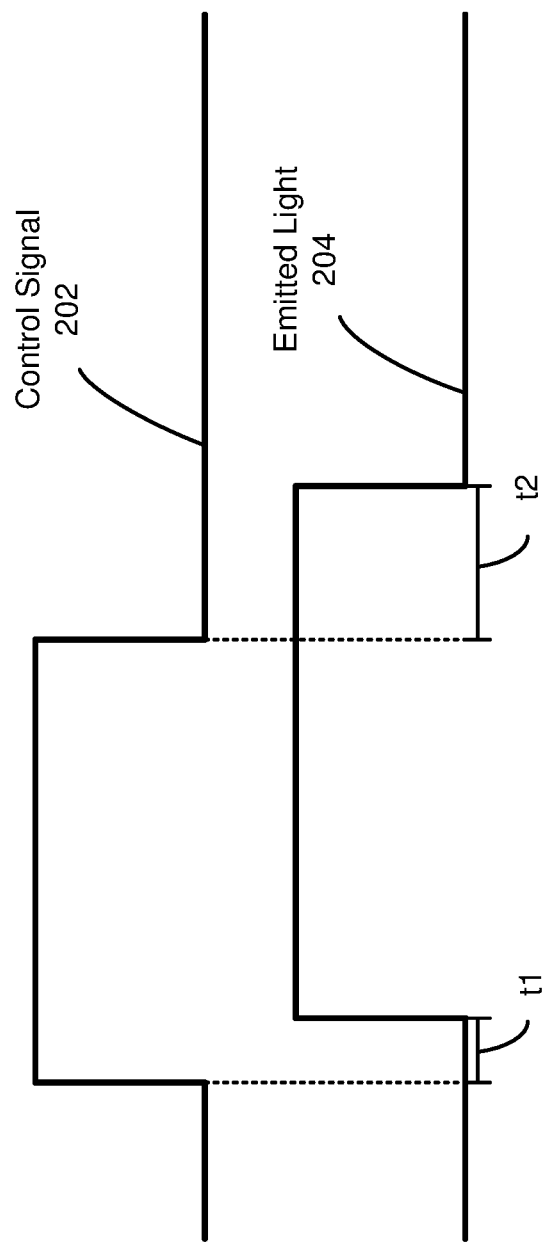
FIG. 2 is a graphical view of the delay and/or jitter between a control signal and emitted light, according to one embodiment.

FIG. 2 illustrates a graphical view of the delay and/or jitter between a control signal 202 and emitted light 204. The control signal 202 may represent a signal provided to a controller or drive circuit, such as the controller 104 or a driver within the light source 102 of FIG. 1. As illustrated, there is a delay of t1 between the control signal 202 going high (e.g., turning on) and light being emitted 204. There is a delay of t2 between the control signal 202 going low (e.g., turning off) and light being emitted 204. For example, the delays t1 and t2 may include some constant delay as well as some non constant variation resulting from the amount of jitter in a controller and/or driver. The amount of jitter or variation in a system or device is described by the jitter specification (jitter spec). For example, if t1 has a value of 1 microsecond then t2 may have a value of 1 microsecond plus or minus the jitter spec of the controller or driver.

Because jitter is not under control of the system or user, the jitter spec represents the amount of unpredictable time variation that may be present. If the jitter spec is too large with respect to a pulse of light, significant reductions in image quality or image brightness variations can result. For example, in a video endoscopic system, different lines or frames within the video or series of images can have a different brightness, leading to flicker and overall reduced video or image quality. For example, if a controller has a jitter spec of 10% of a pulse of light, the pulse of light may vary from 90% of its desired length to 110% of its desired length. This may lead to brightness variations between images or lines of an image within a video of up to ⅓. Furthermore, a large jitter spec may result in light being emitted during readout. If light is emitted during readout, significant variations between pixels and lines may reduce image quality. See, for example, FIG. 2D and associated discussion in U.S. Patent Application Publication No. US 2014/0163319 A1. Thus, if a jitter spec is large enough, a pulse may be limited in size to avoid overlapping into a readout time period of the image sensor 114. Limits on the pulse size may require a reduction in frame rate (increase in time between captured images or larger blanking periods) or may result in reductions in brightness, which may reduce the ability of an image sensor 114 to capture detailed images.

In one embodiment, the controller 104 as in FIG. 1 has a jitter spec small enough to reduce variations in brightness or image quality. In one embodiment, the driver must have a tolerance or jitter spec of about 1 micro second or less. In one embodiment, the tolerance or jitter spec of the driver is about 50 nanoseconds. The reduced jitter spec may be accomplished with a higher clock rate or a more accurate clock in a controller or driver. In one embodiment, the jitter spec is less than the time it takes an image sensor to read out one line (e.g., row or column). For example, a CMOS array may readout pixels from the array line by row or column. In one embodiment, the jitter spec is less than the time it takes an image sensor to read out a single pixel. In one embodiment, the jitter spec may be less than or equal to 10% to 25% of the readout period of the pixel array of the image sensor, or the time it takes an image sensor to read out all the lines in the pixel array. In one embodiment, the jitter spec may be less than or equal to about 10% to about 25% of the readout period of the pixel array of the image sensor, or the time it takes an image sensor to read out all the lines in the pixel array. For example, in a pixel array that comprises a total of 400 lines, the jitter spec is less than or equal to the time that is required to read out 40-100 lines of the 400 lines in the pixel array. Thus, the amount of variation in the light captured may be low enough to reduce image flicker and/or provide as much light as possible between readout periods. For example, with a low jitter spec a control signal to turn off light emission may be provided close to the time at which a readout period begins. The reduced jitter spec and tolerance of the driver thus solves the problem of untoleranced driving causing artifacting in a light pulsing scheme.

In one embodiment, a camera control unit (CCU) may provide signals to a controller or light source to avoid overlapping into a readout period. For example, the CCU may determine a timing for sending a signal to a controller or light source to avoid overlapping into the readout of pixels that are not optical black pixels within the pixel array. In one embodiment, the CCU may maximize the amount of time light is emitted without overlapping into the readout period.

Figure 3:
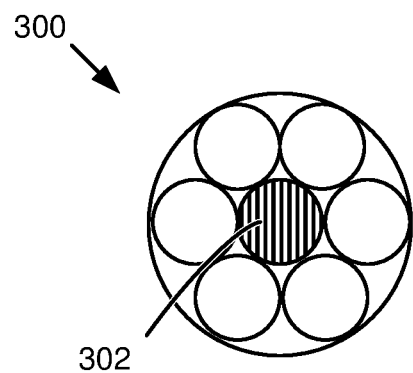
FIG. 3 illustrates a cross section of a fiber bundle having seven fibers with uneven light distribution, according to one embodiment.

FIG. 3 illustrates a cross section of a fiber bundle 300 having seven fibers. The number of fibers is illustrative as any number of fibers may be used. In one embodiment, the number of fibers is limited to reduce a cross sectional area of the fiber bundle. The number of fibers may be based on a number of fibers that provide sufficient light dispersion while allowing for a small cross sectional area since the cross sectional area of an endoscopic lumen may be of importance. In one embodiment, the fiber bundle may include from 2 to 150 fibers. A smaller number of fibers may reduce expense and/or the required cross sectional area needed to carry a fiber bundle. However, increased numbers of fibers improves redundancy. In one embodiment, the fiber bundle includes 5-100 fibers. In one embodiment, the fiber bundle includes 5-50 fibers. In one embodiment, the fiber bundle includes 7-15 fibers. In one embodiment, the fiber bundle includes 7 fibers. When a smaller number of fibers is used, it may be desirable that each fiber receives the same amount of light and/or the same amount of a specific color of light. For example, if light provided to the fiber bundle is mostly in the center, the center fiber may receive the majority of the electromagnetic energy. Thus, an imaging scene may be unevenly illuminated by color or brightness.

FIG. 3 illustrates a center fiber 302 having more or most of the electromagnetic energy. Additionally, if more light enters into one fiber than another, the overall amount of light (power) that can be carried in the fibers is reduced. For example, a fiber may have a burn-out limit or other limit that may result in the fiber melting or otherwise becoming inoperative if light above a certain energy level or intensity is provided to the fiber. Thus, if light is more evenly distributed across fibers, an increase in power and illumination at a scene is possible.

In one embodiment, a light source that provides light to the fiber bundle 300 may mix one or more colors of light before providing to a fiber bundle. For example, the light source 102, jumper waveguide 106, and/or coupler 108 may evenly mix light before providing the light to the lumen waveguide 110. In one embodiment, the light source may include a first laser emitter that emits light of a first wavelength and a second laser emitter that emits light of a second wavelength. The light source may mix the light by having light from the first laser emitter and the second laser emitter enter the jumper waveguide 106 (or other waveguide) at a same or substantially same angle. A same or substantially same angle may be achieved by positioning light sources at a same angle as each other. In one embodiment, a dichroic mirror may allow for a same or substantially same angle by reflecting light of one color (or wavelength) while being transparent to another color (or wavelength) of light. In one embodiment, the light source may include a diffuser, mixing rod, lens, or other optical element to mix light before entry into a fiber optic cable, such as the lumen waveguide 110 of FIG. 1.

In one embodiment, a light source that provides light to the fiber bundle 300 may provide an evenly distributed light intensity to a waveguide. In one embodiment, the peak intensity of light within a region where light is collected for a waveguide may be substantially the same as or close to the average intensity of light over the region. For example, the light provided to a collection region may have a top hat profile so that each fiber collects and/or receives a same or similar intensity of light. The light source may provide or approximate a top hat profile by providing laser light at an angle to a surface of a collection region. For example, emitters may have a Gaussian or other non-constant intensity profile. By angling the emitters in relation to a collection region, the Gaussian profile may be flattened out into a more constant or top-hat profile. The top hat profile may also be generated using lenses, diffusers, mixing rods, or the like.

Figure 4:
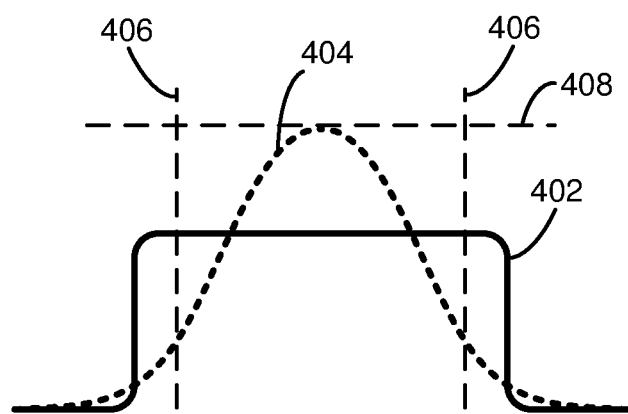
FIG. 4 is a graphical view of a top hat profile and a Gaussian profile, according to one embodiment.

FIG. 4 graphically illustrates a top hat profile 402 and a Gaussian profile 404. The horizontal axis represents horizontal distance and the vertical axis represents light intensity. The lines 406 represent the boundaries or width of a collection region or fiber bundle. Line 408 represents a burn-out level for a fiber or other waveguide. For example, the line 408 may represent a burn-out level for a plastic fiber. With the Gaussian profile 404, most of the light will end up in a center fiber. Because most of the light is in the center fiber other fibers may be far below the burn-out level. With the top-hat profile, all fibers will be at the same level, whether it be near the burn-out level or below it. For example, with the top hat profile 402, the total amount of energy carried by a fiber bundle may be significantly increased because each bundle can be placed near burn-out without risking burn-out of any single fiber. For example, with the Gaussian profile 404 an increase in the total amount of power could lead to a center fiber significantly exceeding the burn-out level with the edge fibers far below the burn-out level. FIG. 4 clearly illustrates that more power can be provided before any of the individual fibers reach burn-out using a top-hat profile. For example, the Gaussian profile 404 and the top-hat profile 402 may provide the same amount of wattage to the fiber bundle, while the top-hat profile 402 can still be increased significantly before reaching burn-out. Thus, a significant improvement in the total amount of light delivered using plastic fibers can be achieved. In some cases a 50% or greater increase of wattage carried by a fiber bundle may be achieved. In an embodiment, the plastic fibers may have a burn-out energy level for light/electromagnetic energy emitted by the one or more emitters above which damage to the plastic fibers may occur, wherein the light energy is spread out across the plurality of plastic fibers to allow a greater amount of energy to be carried by a fiber bundle including the plastic fibers without reaching the burn-out energy level in any of the plastic fibers.

In one embodiment, mixing and a top-hat profile may be implemented by a light source for use with plastic fiber bundles. For example, the light source 102 and/or the jumper waveguide 106 may not include plastic waveguides. However, the light source 102 may provide mixing and a top-hat profile to allow for use with a fiber bundle, such as a plastic fiber bundle, at the lumen waveguide 110. In one embodiment, the use of mixing and/or a top-hat profile may allow for greater power delivery in view of losses that may be incurred when moving the light between different materials (e.g., from a diffuser to a glass fiber, to a plastic fiber, and/or back to a glass fiber or diffuser). For example, the greater power delivery may offset losses in previous or subsequent transitions so that sufficient light can still be delivered to a scene for illumination.

Figure 5:
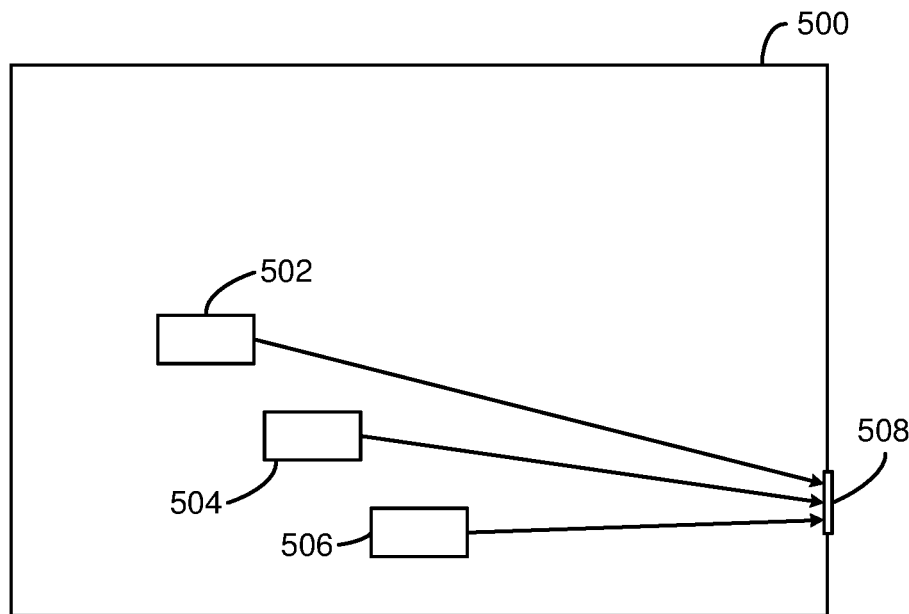
FIG. 5 is a schematic block diagram illustrating a light source having a plurality of emitters, according to one embodiment.
Figure 6:
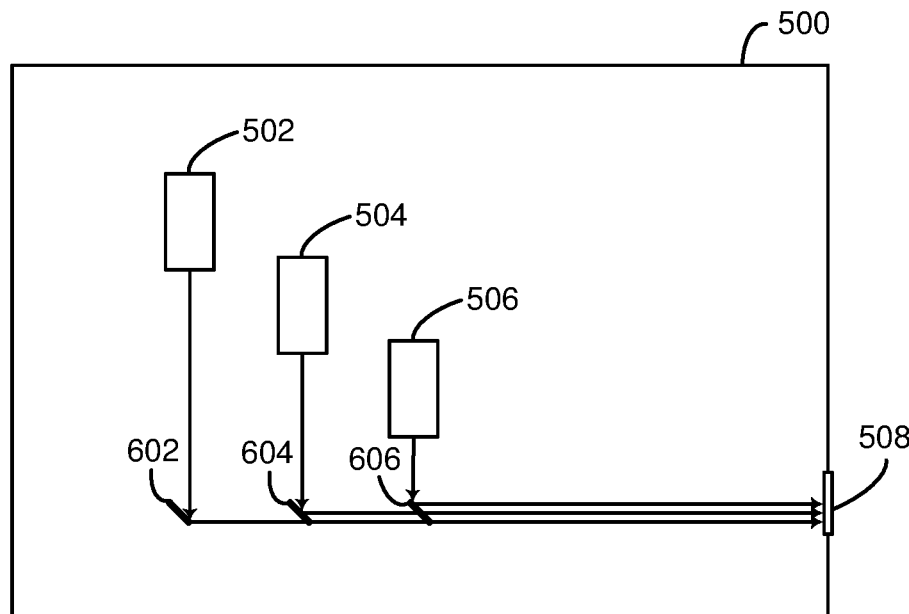
FIG. 6 is a schematic block diagram illustrating a light source having a plurality of emitters, according to another embodiment.
Figure 7:
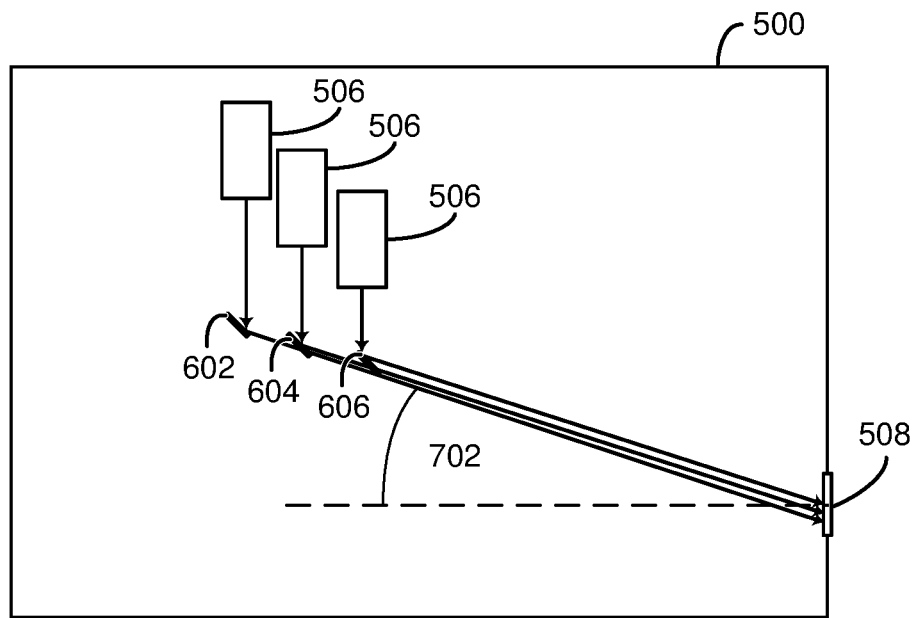
FIG. 7 is a schematic block diagram illustrating a light source having a plurality of emitters, according to yet another embodiment.

FIGS. 5-7 are schematic block diagrams illustrating a light source 500 having a plurality of emitters. With regard to FIG. 5, the emitters include a first emitter 502, a second emitter 504, and a third emitter 506. The emitters 502, 504, and 506 may include one or more laser emitters that emit light having different wavelengths. For example, the first emitter 502 may emit a wavelength that is consistent with a blue laser, the second emitter 504 may emit a wavelength that is consistent with a green laser, and the third emitter 506 may emit a wavelength that is consistent with a red laser. The emitters 502, 504, 506 emit lasers toward a collection region 508, which may be the location of a waveguide, lens, or other optical component for collecting and/or providing light to a waveguide, such as the jumper waveguide 106 or lumen waveguide 110 of FIG. 1.

In the embodiment of FIG. 5, the emitters 502, 504, 506 each deliver laser light to the collection region 508 at different angles. The variation in angle can lead to variations where electromagnetic energy is located in an output waveguide. For example, if the light passes immediately into a fiber bundle (glass or plastic) at the collection region 508, the varying angles may cause different amounts of light to enter different fibers. For example, the angle may result in intensity variations across the collection region 508. Furthermore, light from the different emitters would not be homogenously mixed so some fibers may receive different amounts of light of different colors. As discussed previously, variation in the color or intensity of light in different fibers can lead to non-optimal illumination of a scene. For example, variations in delivered light or light intensities may result at the scene and captured images.

In one embodiment, an intervening optical element may be placed between a fiber bundle and the emitters 502, 504, 506 to mix the different colors (wavelengths) of light before entry into the fibers. Example intervening optical elements include a diffuser, mixing rod, one or more lenses, or other optical components that mix the light so that a given fiber receive a same amount of each color (wavelength). For example, each fiber in the fiber bundle may have a same color. This mixing may lead to the same color in each fiber but may, in some embodiments, still result in different total brightness delivered to different fibers. In one embodiment, the intervening optical element may also spread out or even out the light over the collection region so that each fiber carries the same total amount of light (e.g., see the top hat profile 402 of FIG. 4).

Although the collection region 508 is represented as a physical component in FIG. 5, the collection region 508 may simply be a region where light from the emitters 502, 504, and 506 is delivered. In some cases, the collection region 508 may include an optical component such as a diffuser, mixing rod, lens, or any other intervening optical component between the emitters 502, 504, 506 and an output waveguide.

FIG. 6 illustrates an embodiment of a light source 500 with emitters 502, 504, 506 that provide light to the collection region 508 at the same or substantially same angle. The light is provided at an angle substantially perpendicular to the collection region 508. The light source 500 includes a plurality of dichroic mirrors including a first dichroic mirror 602, a second dichroic mirror 604, and a third dichroic mirror 606. The dichroic mirrors 602, 604, 606 include mirrors that reflect a first wavelength of light, but transmit (or are transparent to) a second wavelength of light. For example, the third dichroic mirror 606 may reflect blue laser light provided by the third emitter, while being transparent to the red and green light provided by the first emitter 502 and the second emitter 504, respectively. The second dichroic mirror 604 may be transparent to red light from the first emitter 502, but reflective to green light from the second emitter 504.

Because the dichroic mirrors allow other wavelengths to transmit or pass through, each of the wavelengths may arrive at the collection region 508 from a same angle and/or with the same center or focal point. Providing light from the same angle and/or same focal/center point can significantly improve reception and color mixing at the collection region 508. For example, a specific fiber may receive the different colors in the same proportions they were transmitted/reflected by the emitters 502, 504, 506 and mirrors 602, 604, 606. Light mixing may be significantly improved at the collection region compared to the embodiment of FIG. 5. In one embodiment, any optical components discussed herein may be used at the collection region 508 to collect light prior to providing it to a fiber bundle.

FIG. 7 illustrates an embodiment of a light source 500 with emitters 502, 504, 506 that also provide light to the collection region 508 at the same or substantially same angle. However, the light incident on the collection region 508 is offset from being perpendicular. Angle 702 indicates the angle offset from perpendicular (i.e., a non-perpendicular angle). In one embodiment, the laser emitters 502, 504, 506 may have cross sectional intensity profiles that are Gaussian. As discussed previously, improved distribution of light energy between fibers may be accomplished by creating a more flat or top-hat shaped intensity profile. In one embodiment, as the angle 702 is increased, the intensity across the collection region 508 approaches a top hat profile. For example, a top-hat profile may be approximated even with a non-flat output beam by increasing the angle 702 until the profile is sufficiently flat.

The top hat profile may also be accomplished using one or more lenses, diffusers, mixing rods, or any other intervening optical component between the emitters 502, 504, 506 and an output waveguide or fiber optic bundle.

Figure 8:
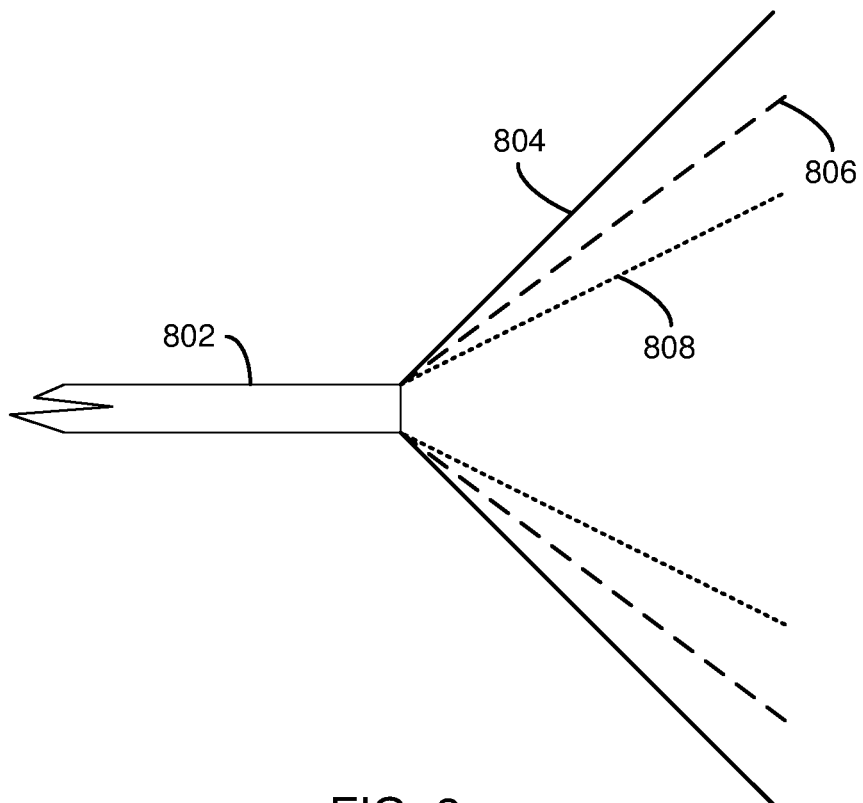
FIG. 8 is a schematic side view illustrating light output from an optical fiber, according to one embodiment.

FIG. 8 is a schematic side view illustrating light output from an optical fiber 802 in comparison to a camera field of view. In one embodiment, a plastic fiber has a numerical aperture of 0.63 with a field of view of 100 degrees, as indicated by dashed line 806, and a glass fiber has a numerical aperture of 0.87 with a field of view of 120 degrees, as indicated by solid line 804. However, light emitted within the field of view has an approximately Gaussian profile within a light cone that is less than the field of view. For example, nearly all the light for a plastic fiber may be within a cone of 80 degrees, as indicated by dotted line 808. Thus, a center region of an image may be too bright while the edges are too dark. This problem is worse when plastic fiber is used, for example, when the lumen waveguide includes plastic fibers.

Figure 9:
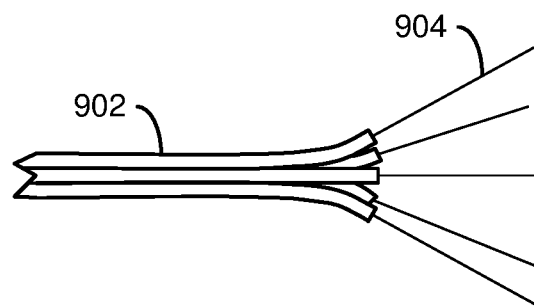
FIG. 9 is a schematic diagram illustrating aiming of fibers of a fiber bundle at an output end, according to one embodiment.

In one embodiment, a more uniform distribution of light can be achieved by aiming the ends of the fibers where light exits the fiber bundle. FIG. 9 is a schematic diagram illustrating aiming of fibers, such as plastic fibers, of a fiber bundle 902 at an output end. Aiming the fibers away from a center may broaden the cone in a field of view with no light loss at the output. An end of each fiber may be held in a desired position to distribute the light where the combination of light cones from the fibers provides a more even illumination. A fiber bundle 902 includes a plurality of fibers and lines 904 that indicate the orientation of cones output by the individual fibers. For example, a fixture may be used to hold the ends of fibers at a physical mold, sheet with holes, or the like that may hold the fibers in the desired orientation. The fibers may be oriented in an optimal orientation for even illumination of a scene. The tips of the fibers in the fiber bundle may be located near a scope tip and may be pointed to spread light around a region centered on the focal point or camera lens axis.

Figure 10:
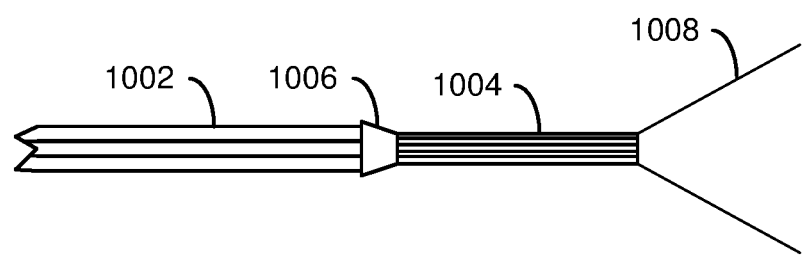
FIG. 10 is a schematic diagram illustrating output of light using glass fibers, according to one embodiment.

FIG. 10 is a schematic diagram illustrating output of light using glass fibers 1004. Specifically, a lumen waveguide may include plastic fibers 1002 and then transition to glass fibers 1004 at or near an output. The glass fibers 1004 generally have a higher numerical aperture and a wider field of view than plastic fibers. Thus, a wider and more even distribution of light energy may be achieved. The light traveling through the plastic fibers 1002 may be guided to the glass fibers 1004 via connector 1006 or connecting waveguide. The light output from the glass fibers 1004 may have a wide light cone 1008, as compared to the light cone for a plastic fiber, for improved illumination of a scene. The coupling may occur in a hand piece or in a lumen of the arthroscope. For example, the connector 1006 may be positioned in a hand piece or in a lumen to limit the amount of glass fibers 1004 used. Moving from plastic fiber through a taper in the hand piece or the lumen to a glass fiber that has a higher numerical aperture (e.g., NA of 0.84-0.87) may result is the same field of view as a conventional athro scope. However, light loss may be significant, such as about 25% compared to the aiming embodiment, which experiences no light loss at the output.

Figure 11:
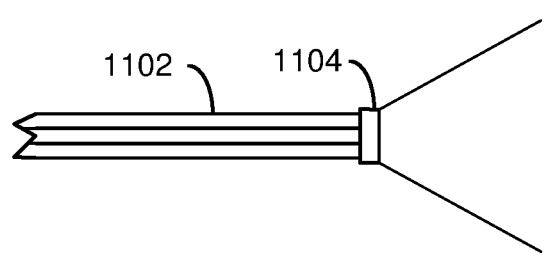
FIG. 11 is a schematic diagram illustrating output of light using a diffuser at an output, according to one embodiment.

FIG. 11 is a schematic diagram illustrating output of light using a diffuser 1104 at an output. Specifically, a lumen waveguide may include plastic fibers 1102 and then transition to the diffuser 1104 at or near an output. The diffuser 1104 may include any type of optical diffuser, mixing rod, or the like. Example diffusers include a holographic diffuser from Edmund®, Luminit®, or an RPC Engineered Diffuser™. The diffuser at the output can produce an even larger angle than the use of class fibers, but is less efficient, such as about 40-60% efficient versus the aiming embodiment.

In one embodiment, plastic fibers 1002 are significantly cheaper than glass fibers 1004. The reduced price can lead to significantly cheaper illumination system and endoscopic system. Because glass may only be used for a short distance near an output, or not at all, a significant cost savings may be achieved. For example, this cost savings of plastic may still be achieved in the embodiment of FIG. 10 because the amount (length and number) of glass fibers 1004 is significantly reduced. Although significant amounts of light may be lost in the transition from plastic to glass (e.g., 25% loss), or using a diffuser (e.g., 40-60% light loss) the usage of the top-hat profile or other methods herein may still allow for sufficient lighting to be delivered to an imaging region because a greater amount of light may be carried in the fibers when compared to other methods or devices. For example, the other methods and devices discussed herein in relation may be used in combination to provide an overall cheaper endoscopic illumination system while maintaining sufficient lighting for high image quality. In one embodiment, a portion of the endoscopic system, such as the lumen waveguide 110 of FIG. 1, may be disposable or reposable.

It should be understood that embodiments for outputting light may include a combination of the embodiments of FIGS. 9-11. For example, plastic fibers may be transitioned to glass fibers and the glass fibers may be aimed to provide more uniform and improved illumination.

Figure 12:
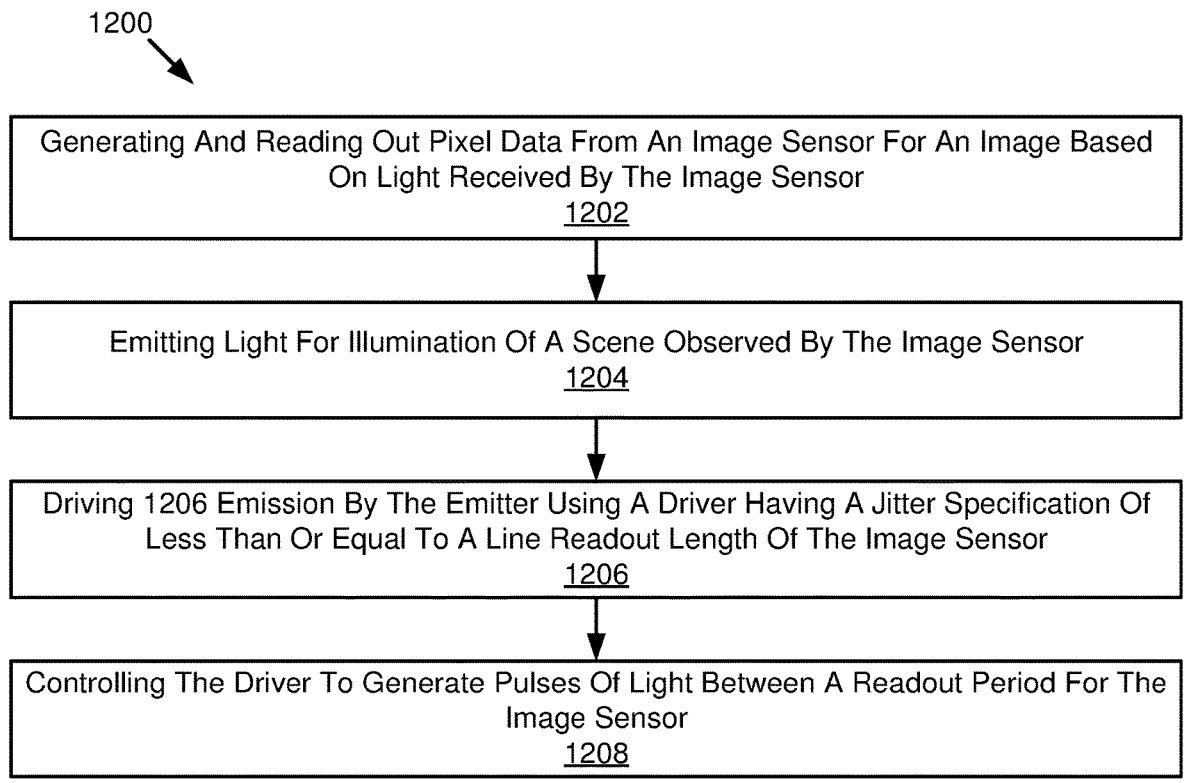
FIG. 12 is a schematic flow chart diagram illustrating a method for providing light to an imaging scene in a light deficient environment, according to one embodiment.

FIG. 12 is a schematic flow chart diagram illustrating an example method 1200 for providing light to an imaging scene in a light deficient environment. The method 1200 may be performed by an illumination system, such as the system 100 of FIG. 1.

The method 1200 begins and an image sensor generates and reads out at 1202 pixel data from an image sensor for an image based on light received by the image sensor, wherein a time length for reading out a line of pixel data includes a line readout length. An emitter emits at 1204 light for illumination of a scene observed by the image sensor. A driver drives at 1206 emission by the emitter, wherein the driver includes a jitter specification of less than or equal to the line readout length. A controller controls at 1208 the driver to drive the emitter to generate pulses of light between readout periods for the image sensor.

Figure 13:
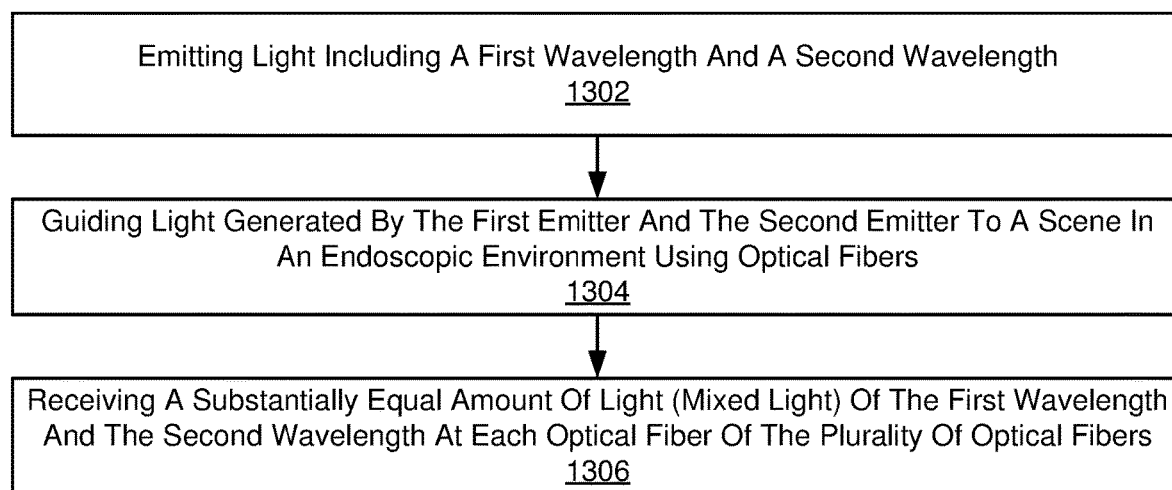
FIG. 13 is a schematic flow chart diagram illustrating a method for providing light to an imaging scene in a light deficient environment, according to another embodiment.

FIG. 13 is a schematic flow chart diagram illustrating an example method 1300 for providing light to an imaging scene in a light deficient environment. The method 1300 may be performed by an illumination system, such as the system 100 of FIG. 1.

The method 1300 begins and a first emitter and second emitter emit at 1302 light including a first wavelength and a second wavelength. A plurality of optical fibers guides at 1304 light generated by the first emitter and the second emitter to a scene in an endoscopic environment. The plurality of optical fibers receives at 1306 a substantially equal amount of light (mixed light) from the first emitter and the second emitter at each optical fiber of the plurality of optical fibers.

Figure 14:
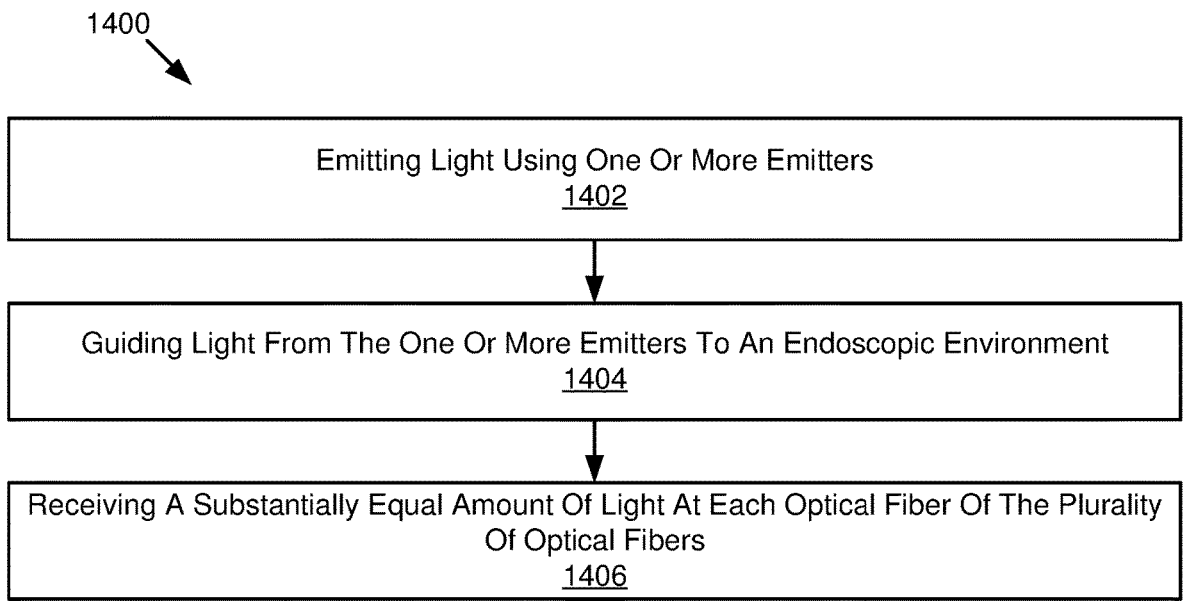
FIG. 14 is a schematic flow chart diagram illustrating a method for providing light to an imaging scene in a light deficient environment, according to another embodiment.

FIG. 14 is a schematic flow chart diagram illustrating an example method 1400 for providing light to an imaging scene in a light deficient environment. The method 1400 may be performed by an illumination system, such as the system 100 of FIG. 1.

The method 1400 begins and one or more emitters emit light at 1402. A plurality of optical fibers guides at 1404 light from the one or more emitters to an endoscopic environment. Each optical fiber of the plurality of optical fibers receives at 1406 a substantially equal amount of light from the one or more emitters.

Figure 15:
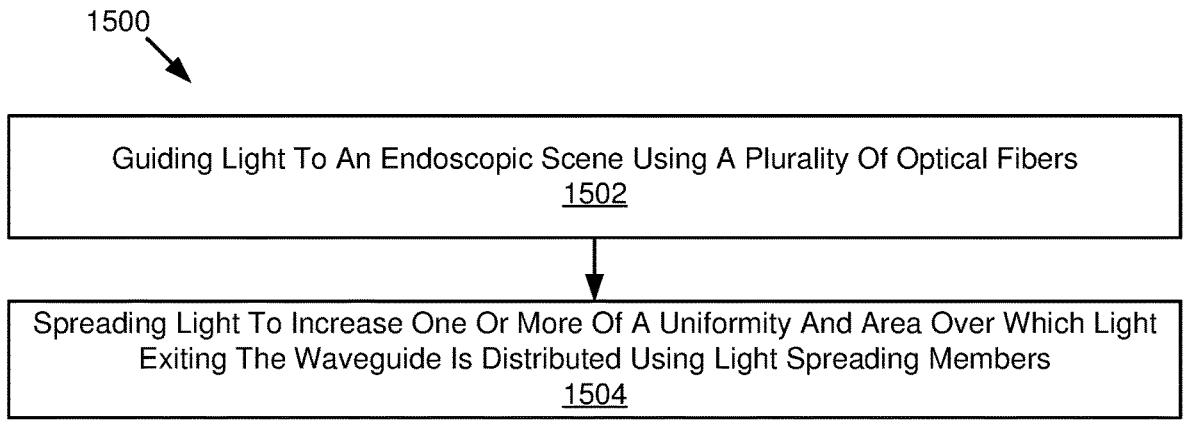
FIG. 15 is a schematic flow chart diagram illustrating a method for providing light to an imaging scene in a light deficient environment, according to yet another embodiment.

FIG. 15 is a schematic flow chart diagram illustrating an example method 1500 for providing light to an imaging scene in a light deficient environment. The method 1500 may be performed by an illumination system, such as the system 100 of FIG. 1.

The method 1500 begins and a plurality of optical fibers guides at 1502 light to an endoscopic scene. A light spreading member spreads at 1504 light to increasing one or more of a uniformity and area over which light exiting the waveguide is distributed.

In one embodiment, a single fiber may replace a fiber bundle (such as a fiber bundle as in any of FIG. 3, 9, 10, or 11). The single fiber may be larger and may be able to handle a larger amount of power than a bundle of smaller fibers for the same occupied cross-sectional area. The single fiber may extend from a console and through a lumen to provide light to an interior of a body, or other light deficiency environment. For example, the single fiber may operate as a lumen waveguide that extends from a light source 102 or jumper waveguide 106 and through a lumen 112 (see FIG. 1). Light may be provided by the light source 102 directly to the single fiber with a top-hat profile.

Because a plastic fiber may only have a numerical aperture of 0.63 or 0.65, most of the light may only come out at an angle of 70 or 80 degrees. At an output of the single fiber (e.g., at a distal end of a lumen), a diffuser may be positioned to spread output light and create a more even illumination within a field-of-view of a camera that captures images. In one embodiment, the type of diffuser or the presence of a diffuser may be based on the field-of-view used by the camera during the examination. For example, laparoscopic procedures or examinations may allow for more narrow fields of view (such as 70 degrees) while arthroscopic procedures or examinations may use broader fields of view (such as 110 degrees). Thus, a diffuser may be used for arthroscopic examinations or lumens while a diffuser may be absent for laparoscopic examinations or lumens. For example, light may be emitted from the fiber into the interior environment without passing through a diffuser in the laparoscopic examination or lumen.

Figures 16, 17:
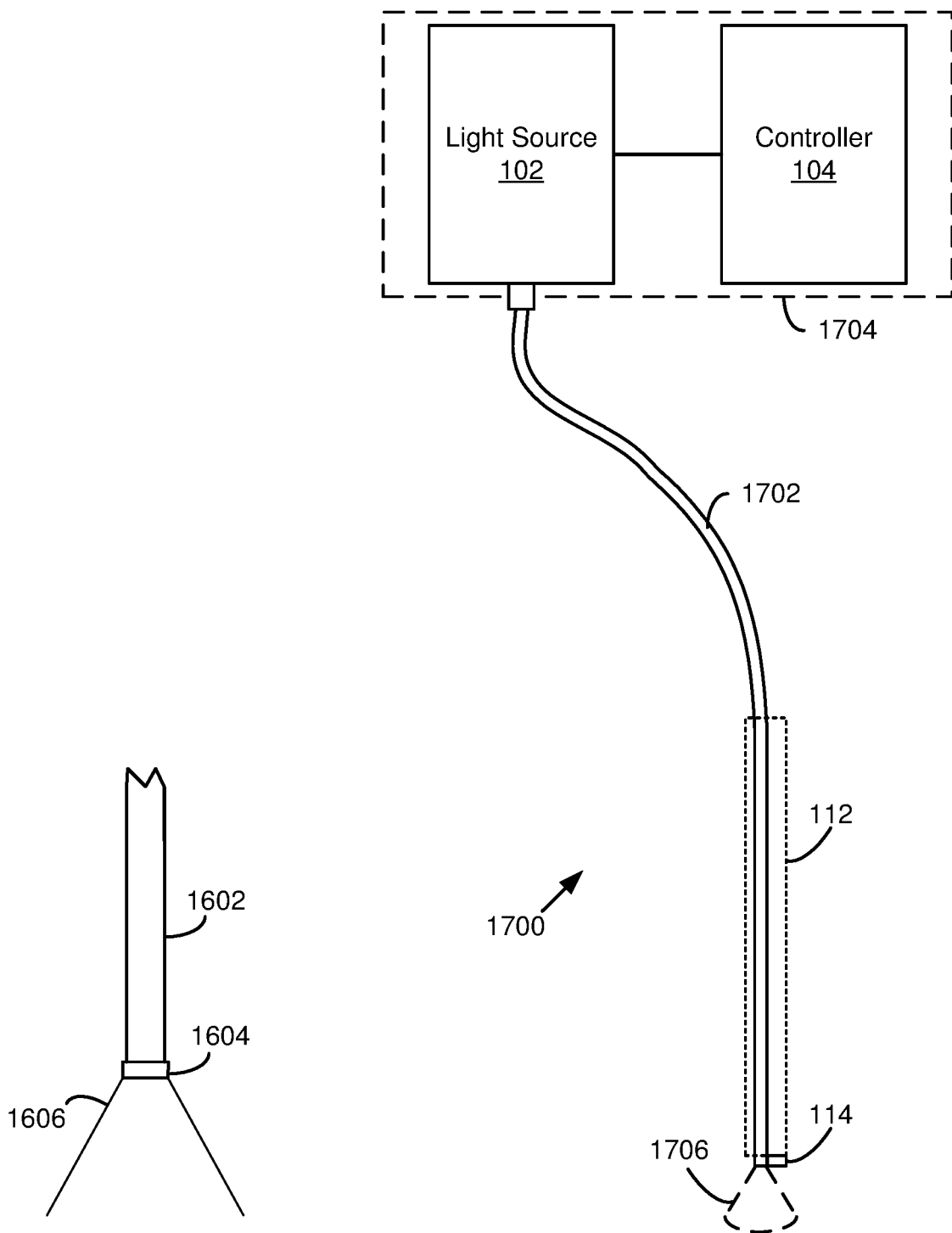
FIG. 16 is a schematic diagram illustrating a single optical fiber outputting via a diffuser at an output according to one embodiment.
FIG. 17 is a schematic diagram illustrating a system for providing illumination to a light deficient environment according to one embodiment.

FIG. 16 is a schematic diagram illustrating a single optical fiber 1602 outputting via a diffuser 1604 at an output. In one embodiment, the optical fiber 1602 may have a diameter of 500 microns and have a numerical aperture of 0.65 and emits a light cone 1606 of about 70 or 80 degrees without a diffuser 1604. With the diffuser, the light cone 1606 may have an angle of about 110 or 120 degrees.

FIG. 17 is a schematic diagram illustrating an example embodiment of a system 1700 for providing illumination to a light deficient environment, such as for endoscopic imaging. The system 1700 includes a light source 102, a controller 104, a lumen waveguide 1702, a lumen 112, and an image sensor 114 with accompanying optical components. In one embodiment, the light source 102 and/or the controller 104 may be located in a console or camera control unit 1704 to which an endoscope comprising the lumen 112 may be attached.

The light source 102 generates light or other electromagnetic energy that is provided into the lumen waveguide 1702 using any embodiment or method discussed herein. The electromagnetic energy travels through the lumen waveguide 1702 to illuminate a scene at a distal end of the lumen 112. The lumen 112 may be inserted into a patient's body for imaging, such as during a procedure or examination. The light is output as illustrated by dashed lines 1706. A scene illuminated by the light may be captured using the image sensor 114 and displayed for a doctor or some other medical personnel.

In one embodiment, the lumen waveguide 1702 may include a single plastic optical fiber of about 500 microns. The plastic fiber may be low cost but the width may allow the fiber to carry a sufficient amount of light to a scene, with coupling, diffuser, or other losses. The lumen waveguide 110 includes a plurality of optical fibers. The lumen waveguide 1702 may receive light directly from the light source or via a jumper waveguide (e.g., see the jumper waveguide 106 of FIG. 1). A diffuser may be used to broaden the light output 1706 for a desired field of view of the image sensor 114 or other optical components.

EXAMPLES

The following examples pertain to further embodiments.

Example 1 is an endoscopic system that includes an image sensor. The image sensor includes a pixel array and is configured to generate and read out pixel data for an image based on electromagnetic radiation received by the pixel array. The pixel array includes a plurality of lines for reading out pixel data, wherein a time length for reading out all the plurality of lines of pixel data in the pixel array comprises a readout period. The endoscopic system includes an emitter configured to emit electromagnetic radiation for illumination of a scene observed by the image sensor. The endoscopic system includes an electromagnetic radiation driver configured to drive emissions by the emitter, wherein the electromagnetic radiation driver includes a jitter specification that is less than or equal to about 10% to about 25% percent of the readout period of the pixel array of the image sensor.

In Example 2, the endoscopic system of Example 1 further includes a controller configured to control the electromagnetic radiation driver to drive the emitter to generate one or more pulses of electromagnetic radiation between a readout period for the image sensor.

In Example 3, the controller of Example 2 is further configured to determine a timing for signals to the electromagnetic radiation driver to pulse electromagnetic radiation for illuminating a scene in an endoscopic environment without overlapping into the readout period for the image sensor.

In Example 4, the readout period as in any of Examples 2-3 starts after reading out a row or column of optical black pixels and the readout period ends with the readout of a row or column of optical black pixels.

In Example 5, a time length for reading out pixel data for a single pixel in any of Examples 1-5 is a pixel readout length, wherein the electromagnetic radiation driver jitter specification is less than or equal to the pixel readout length of the image sensor.

In Example 6, the image sensor as in any of Examples 1-5 includes a complementary metal-oxide-semiconductor (CMOS) image sensor.

In Example 7, the CMOS image sensor as in any of Examples 1-6 is monochromatic.

In Example 8, the CMOS image sensor as in any of Examples 1-6 is color filtered.

In Example 9, the emitter as in any of Examples 1-8 includes one or more pulsing lasers.

In Example 10, the electromagnetic radiation driver jitter specification as in any of Examples 1-9 is about 1 microsecond or less.

In Example 11, the electromagnetic radiation driver jitter specification as in any of Examples 1-9 is about 50 nanoseconds or less.

In Example 12, the image sensor as in any of Examples 1-5 includes a charge-coupled device (CCD) image sensor.

In Example 13, the CCD image sensor as in any of Examples 1-5 and 12 is monochromatic.

In Example 14, the CCD image sensor as in any of Examples 1-5 and 12 is color filtered.

In Example 15, the emitter as in any of Examples 1-14 emits a plurality of pulses of electromagnetic radiation, wherein each successive pulse is a different range of wavelengths of electromagnetic energy.

In Example 16, the system as in any of Examples 1-15 includes an endoscope comprising a lumen with a distal end, wherein the image sensor is located within the distal end of the lumen of the endoscope.

In Example 17, the system as in any of Examples 1-4 and 6-16 wherein a time length for reading out a single line of pixel data comprises a line readout length, wherein the jitter specification is less than or equal to the line readout length.

Example 18 is a method for endoscopic imaging that may be used alone or with any of Examples 1-17. The method includes generating and reading out pixel data for an image based on electromagnetic radiation received by a pixel array of an image sensor. The pixel array comprises a plurality of lines for reading out pixel data, and wherein a time length for reading out all the plurality of lines of pixel data in the pixel array comprises a readout period. The method also includes emitting electromagnetic radiation using an emitter. The method further includes illuminating a scene observed by the image sensor with the electromagnetic radiation emitted from the emitter. The method further includes driving emission by the emitter using an electromagnetic radiation driver, the electromagnetic radiation driver comprising a jitter specification that is less than or equal to about 10% to about 25% percent of the readout period of the pixel array of the image sensor.

In Example 19, the method as in Example 18 further includes controlling the electromagnetic radiation driver to drive the emitter to generate one or more pulses of electromagnetic radiation between a readout period for the image sensor using a controller.

In Example 20, the method as in any of Examples 18 and 19 wherein the controller determines a timing for signals to the electromagnetic radiation driver to pulse electromagnetic radiation for illuminating a scene in an endoscopic environment without overlapping into the readout period for the image sensor.

In Example 21, the method as in any of Examples 18-20 wherein the readout period starts after reading out a row or column of optical black pixels and the readout period ends with the readout of a row or column of optical black pixels.

In Example 22, the method as in any of Examples 18-21 wherein a time length for reading out pixel data for a single pixel is a pixel readout length, wherein the jitter specification is less than or equal to the pixel readout length of the image sensor.

In Example 23, the method as in any of Examples 18-22 wherein the image sensor comprises a complementary metal-oxide-semiconductor (CMOS) image sensor.

In Example 24, the method as in any of Examples 18-23 wherein the CMOS image sensor is monochromatic.

In Example 25, the method as in any of Examples 18-23 wherein the CMOS image sensor is color filtered.

In Example 26, the method as in any of Examples 18-25 wherein the emitter comprises one or more pulsing lasers.

In Example 27, the method as in any of Examples 18-26 wherein the electromagnetic radiation driver jitter specification is about 1 microsecond or less.

In Example 28, the method as in any of Examples 18-27 wherein the electromagnetic radiation driver jitter specification is about 50 nanoseconds or less.

In Example 29, the method as in any of Examples 18-22 and 26-28 wherein the image sensor is a charge-coupled device (CCD) image sensor.

In Example 30, the method as in any of Examples 18-22 and 26-29 wherein the CCD image sensor is monochromatic.

In Example 31, the method as in any of Examples 18-22 and 26-29 wherein the CCD image sensor is color filtered.

In Example 32, the method as in any of Examples 18-31 further includes emitting a plurality of pulses of electromagnetic radiation with the emitter, wherein each successive pulse is a different range of wavelengths of electromagnetic energy.

In Example 33, the method as in any of Examples 18-32 wherein the image sensor is located within a distal end of a lumen of an endoscope.

In Example 34, the method as in any of Examples 18-21 and 23-33 wherein a time length for reading out a single line of pixel data comprises a line readout length, wherein the jitter specification is less than or equal to the line readout length.

Example 35 is an endoscopic light source that may be used alone or with any of Examples 1-34. The endoscopic light source includes a first emitter which emits light of a first wavelength at a first dichroic mirror which reflects the light of the first wavelength to a plurality of optical fibers. The endoscopic light source also includes a second emitter which emits light of a second wavelength at a second dichroic mirror which reflects the light of the second wavelength to the plurality of optical fibers. The first dichroic mirror is transparent to the light of the second wavelength.

In Example 36, the first dichroic mirror as in Example 35 reflects light of the first wavelength into the plurality of optical fibers at an angle that is substantially perpendicular to the first emitter.

In Example 37, the second dichroic mirror as in any of Examples 35-36 reflects light of the second wavelength into the plurality of optical fibers through the first dichroic mirror at an angle that is substantially perpendicular to the second emitter.

In Example 38, the first dichroic mirror as in any of Examples 35-37 reflects light of the first wavelength into the plurality of optical fibers at an angle that is offset from perpendicular.

In Example 39, the second dichroic mirror as in any of Examples 35-38 reflects light of the second wavelength into the plurality of optical fibers at an angle through the first dichroic mirror at an angle that is offset from perpendicular.

In Example 40, the endoscopic light source as in any of Examples 35-39 further includes a third emitter which emits light of a third wavelength at a third dichroic mirror which reflects the light of the third wavelength to the plurality of optical fibers.

In example 41, the first dichroic mirror and the second dichroic mirror as in any of Examples 35-40 are transparent to the light of the third wavelength.

In Example 42, the third dichroic mirror as in any of Examples 35-41 reflects light of the third wavelength into the plurality of optical fibers at an angle that is substantially perpendicular to the third emitter.

In Example 43, the third dichroic mirror as in any of Examples 35-42 reflects light of the third wavelength into the plurality of optical fibers at an angle that is offset from perpendicular.

In Example 44, the light of the third wavelength reflected by the third dichroic mirror as in any of Examples 35-43 is reflected into the plurality of optical fibers through the first dichroic mirror.

In Example 45, the light of the third wavelength reflected by the third dichroic mirror as in any of Examples 35-43 is reflected into the plurality of optical fibers through the second dichroic mirror.

In Example 46, endoscopic light source as in any of Examples 35-45 further includes an intervening optical component, wherein the light of the first wavelength and the light of the second wavelength pass through the intervening optical component before entering the plurality of optical fibers.

In Example 47, the intervening optical component as in any of Examples 35-46 includes a diffuser.

In Example 48, the intervening optical component as in any of Examples 35-46 includes a mixing rod.

In Example 49, the plurality of optical fibers as in any of Examples 35-48 includes a plurality of plastic optical fibers and wherein the intervening optical component includes a plurality of glass fibers.

In Example 50, the endoscopic light source as in any of Examples 35-49 further includes a third emitter which emits light of a third wavelength that is reflected by a third dichroic mirror through the first dichroic mirror and the second dichroic mirror, wherein the light of the first wavelength, the light of the second wavelength, and the light of the third wavelength are mixed by the intervening optical component to provide substantially homogenously colored light to each of the plurality of optical fibers.

In Example 51, the first emitter as in any of Examples 35-50 includes a first laser emitter and the second emitter includes a second laser emitter.

In Example 52, the third emitter as in any of Examples 35-51 includes a third laser emitter.

In Example 53, the plurality of optical fibers as in any of Examples 35-52 includes between 2 and 150 fibers.

In Example 54, one of the first emitter, the second emitter, and the third emitter as in any of Examples 35-53 emits a red light and wherein one of the first emitter, the second emitter, and the third emitter emits a green light, and wherein one of the first emitter, the second emitter, and the third emitter emits a blue light.

Example 55 is an endoscopic system that may be used alone or with any of Examples 1-54. The endoscopic system may include a single optical fiber. The endoscopic system may include a light source which transmits light into the single optical fiber. Further, the endoscopic system may include an image sensor disposed at a distal end of the single optical fiber.

In Example 56, the system as in Example 55 includes a diffuser disposed at a distal end of the single optical fiber.

In Example 57, the diffuser as in any of Examples 55-56 provides a light cone having an angle of between 110 degrees and 120 degrees.

In Example 58, the single optical fiber as in any of Examples 55-57 provides a light cone of between 70 degrees and 80 degrees.

In Example 59, the single optical fiber as in any of Examples 55-58 is a plastic optical fiber.

In Example 60, the single optical fiber as in any of Examples 55-59 has a numerical aperture of 0.63.

In Example 61, the single optical fiber as in any of Examples 55-59 has a numerical aperture of 0.65.

In Example 62, the single optical fiber as in any of Examples 55-61 has a diameter of between 475 and 525 microns.

In Example 63, the system as in any of Examples 55-62 further includes a light source controller.

In Example 64, the light source and the light source controller as in any of Examples 55-63 are located in a camera control unit.

In Example 65, the single optical fiber as in any of Examples 55-64 is attached to a plurality of optical fibers between the distal end of the single optical fiber and an endoscope.

In Example 66, the plurality of optical fibers as in any of Examples 55-64 is attached to the camera control unit through the endoscope.

In Example 67, light or other electromagnetic energy as in any of Examples 55-65 is transmitted through the single optical fiber to illuminate a scene at a distal end of the single optical fiber.

In Example 68, the single optical fiber as in any of Examples 55-66 is attached to an endoscope.

Examples 69 is an endoscope that may be used alone or with any of Examples 1-68. The endoscope may include a single optical fiber, an image sensor disposed at a distal end of the single optical fiber, and a diffuser disposed at a distal end of the single optical fiber.

In Example 70, the diffuser as in Example 69 provides a light cone of between 110 and 120 degrees at the distal end of the single optical fiber.

In Example 71, the endoscope as in any of Examples 69-70 includes a light source and a light source controller.

In Example 72, the light source and the light source controller as in any of Examples 69-71 are located in a camera control unit.

In Example 73, the single optical fiber as in any of Examples 69-72 is attached to a plurality of optical fibers between the distal end of the single optical fiber and the light source.

In Example 74, light or other electromagnetic energy as in any of Examples 69-73 is transmitted through the single optical fiber to illuminate a scene at a distal end of the single optical fiber.

In Example 75, the plurality of optical fibers as in Examples 73 includes from 5 to 100 fibers.

Example 76 is an apparatus including means to perform a method or implement an apparatus as in of any of Examples 1-75.

Example 77 is an embodiment comprising any combination of elements, functionality, or devices of Examples 1-76.

Various techniques, or certain aspects or portions thereof, may take the form of program code (i.e., instructions) embodied in tangible media, such as floppy diskettes, CD-ROMs, hard drives, a non-transitory computer readable storage medium, or any other machine readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, an EPROM, a flash drive, an optical drive, a magnetic hard drive, or another medium for storing electronic data. One or more programs that may implement or utilize the various techniques described herein may use an application programming interface (API), reusable controls, and the like. Such programs may be implemented in a high-level procedural or an object-oriented programming language to communicate with a computer system. However, the program(s) may be implemented in assembly or machine language, if desired. In any case, the language may be a compiled or interpreted language, and combined with hardware implementations.

It should be understood that many of the functional units described in this specification may be implemented as one or more components, which is a term used to more particularly emphasize their implementation independence. For example, a component may be implemented as a hardware circuit comprising custom very large scale integration (VLSI) circuits or gate arrays, off-the-shelf semiconductors such as logic chips, transistors, or other discrete components. A component may also be implemented in programmable hardware devices such as field programmable gate arrays, programmable array logic, programmable logic devices, or the like.

Components may also be implemented in software for execution by various types of processors. An identified component of executable code may, for instance, comprise one or more physical or logical blocks of computer instructions, which may, for instance, be organized as an object, a procedure, or a function. Nevertheless, the executables of an identified component need not be physically located together, but may comprise disparate instructions stored in different locations that, when joined logically together, comprise the component and achieve the stated purpose for the component.

Indeed, a component of executable code may be a single instruction, or many instructions, and may even be distributed over several different code segments, among different programs, and across several memory devices. Similarly, operational data may be identified and illustrated herein within components, and may be embodied in any suitable form and organized within any suitable type of data structure. The operational data may be collected as a single data set, or may be distributed over different locations including over different storage devices, and may exist, at least partially, merely as electronic signals on a system or network. The components may be passive or active, including agents operable to perform desired functions.

Reference throughout this specification to "an example" means that a particular feature, structure, or characteristic described in connection with the example is included in at least one embodiment of the present disclosure. Thus, appearances of the phrase "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on its presentation in a common group without indications to the contrary. In addition, various embodiments and examples of the present disclosure may be referred to herein along with alternatives for the various components thereof. It is understood that such embodiments, examples, and alternatives are not to be construed as de facto equivalents of one another, but are to be considered as separate and autonomous representations of the present disclosure.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered illustrative and not restrictive.

Those having skill in the art will appreciate that many changes may be made to the details of the above-described embodiments without departing from the underlying principles of the disclosure.

What is claimed is:

1. An endoscopic system, comprising:
    an endoscope comprising:
        a lumen; and
        an image sensor disposed at a distal end of the lumen;
    a laser light source, comprising two or more lasers, that emits electromagnetic radiation and that is disposed remotely from the endoscope; and
    a waveguide that guides electromagnetic radiation emitted from the laser light source to the distal end of the lumen, the waveguide comprising a single optical fibre having a proximal end and a distal end;
    wherein the distal end of the single optical fibre is disposed at the distal end of the lumen and the proximal end of the single optical fibre is disposed at the laser light source;
    wherein the laser light source emits electromagnetic radiation into a collection region of the proximal end of the single optical fiber; and
    wherein each of the two or more lasers of the laser light source emits light into the collection region of the proximal end of the single optical fibre at angles that are offset from perpendicular to the collection region.

2. The endoscopic system of claim 1, further comprising a diffuser disposed at a distal end of the single optical fiber.

3. The endoscopic system of claim 2, wherein the diffuser provides a light cone having an angle of between 110 degrees and 120 degrees.

4. The endoscopic system of claim 1, wherein the single optical fibre provides a light cone of between 70 degrees and 80 degrees.

5. The endoscopic system of claim 1, wherein the single optical fibre is a plastic optical fiber.

6. The endoscopic system of claim 1, wherein the single optical fibre has a numerical aperture of 0.63.

7. The endoscopic system of claim 1, wherein the single optical fibre has a numerical aperture of 0.65.

8. The endoscopic system of claim 1, wherein the single optical fibre has a diameter of between 475 and 525 microns.

9. The endoscopic system of claim 1, further comprising a light source controller.

10. The endoscopic system of claim 9, wherein the laser light source and the light source controller are located in a camera control unit.

11. The endoscopic system of claim 10, wherein the single optical fibre is attached to a plurality of optical fibres between the distal end of the single optical fibre and an endoscope.

12. The endoscopic system of claim 11, wherein the plurality of optical fibres is attached to the camera control unit through the endoscope.

13. The endoscopic system of claim 1, wherein the light provided through the single optical fibre illuminates a scene at a distal end of the single optical fiber.

14. The endoscopic system of claim 10, wherein the single optical fibre is attached to an endoscope.

15. An endoscope, comprising:
a lumen;
an image sensor disposed at a distal end of the lumen;
a laser light source, comprising two or more lasers, that emits electromagnetic radiation and that is disposed remotely from the lumen;
a waveguide that guides electromagnetic radiation emitted from the laser light source to the distal end of the lumen, the waveguide comprising a single optical fibre having a proximal end and a distal end; and
a diffuser disposed at the distal end of the single optical fiber, such that the diffuser covers a distal end of the single optical fiber;
wherein the distal end of the single optical fibre is disposed at the distal end of the lumen and the proximal end of the single optical fibre is disposed at the laser light source;
wherein the laser light source emits electromagnetic radiation into a collection region of the proximal end of the single optical fiber; and
wherein each of the two or more lasers of the laser light source emits light into the collection region of the proximal end of the single optical fibre at angles that are offset from perpendicular to the collection region.

16. The endoscope of claim 15, wherein the diffuser provides a light cone of between 110 and 120 degrees at the distal end of the single optical fiber.

17. The endoscope of claim 15, further comprising a light source controller.

18. The endoscope of claim 15, wherein the light source and the light source controller are located in a camera control unit.

19. The endoscope of claim 18, wherein the single optical fibre is attached to a plurality of optical fibres between the distal end of the single optical fibre and the laser light source.

20. The endoscope of claim 15, wherein the light provided through the single optical fibre illuminates a scene at a distal end of the single optical fiber.

* * * * *